United States Patent
Rahn et al.

(10) Patent No.: US 6,921,830 B2
(45) Date of Patent: Jul. 26, 2005

(54) METHOD FOR PURIFYING AN ORGANIC SOLVENT FOR THE PURPOSES OF ABSORPTION OF MALEIC ACID ANHYDRIDE

(76) Inventors: Ralf-Thomas Rahn, Cannabichstr.8, 68167 Mannheim (DE); Alexander Weck, Buttstaedterstr.9, 67251 Freinsheim (DE); Gerd Kaibel, Robert-Bosch-Str.4, 68623 Lampertheim (DE)

( * ) Notice: Subject to any disclaimer, the term of this patent is extended or adjusted under 35 U.S.C. 154(b) by 119 days.

(21) Appl. No.: 10/475,219

(22) PCT Filed: Apr. 22, 2002

(86) PCT No.: PCT/EP02/04414

§ 371 (c)(1),
(2), (4) Date: Oct. 20, 2003

(87) PCT Pub. No.: WO02/085834

PCT Pub. Date: Oct. 31, 2002

(65) Prior Publication Data

US 2004/0127726 A1 Jul. 1, 2004

(30) Foreign Application Priority Data

Apr. 23, 2001 (DE) ......................................... 101 19 737

(51) Int. Cl.$^7$ ............................................. C07D 307/36
(52) U.S. Cl. ........................ 549/262; 549/258; 549/259
(58) Field of Search ................................ 549/262, 258, 549/259

(56) References Cited

U.S. PATENT DOCUMENTS 4,118,403 A    10/1978    White

FOREIGN PATENT DOCUMENTS

| EP | 459 543 | 12/1991 |
| EP | 897 905 | 2/1999 |
| WO | 96/29323 | 9/1996 |

*Primary Examiner*—Bernard Dentz

(57) ABSTRACT

In a process for purifying an organic solvent for the absorption of maleic anhydride from a gaseous mixture, in which the maleic anhydride is separated off from the solvent, a substream is taken from the solvent stream, this substream is distilled and returned to the solvent circuit, the proposed improvement comprises separating off a low-boiling fraction and a high-boiling fraction from the fraction consisting essentially of purified solvent and feeding the fraction consisting essentially of purified solvent back into the solvent stream.

8 Claims, No Drawings

METHOD FOR PURIFYING AN ORGANIC SOLVENT FOR THE PURPOSES OF ABSORPTION OF MALEIC ACID ANHYDRIDE

This application is a 371 of PCT/EP02/04414 filed Apr. 22, 2002.

The present invention relates to a process for purifying an organic solvent for the absorption of maleic anhydride from a gaseous mixture.

In the industrial preparation of maleic anhydride (MA), which is nowadays carried out predominantly by oxidation of n-butane by means of air or oxygen in the gas phase, MA is separated from the offgas by absorption. The MA can be absorbed into water or, as is generally considered more favorable, into an organic solvent. Suitable solvents are described, for example, in WO 96/29323.

After absorption has occurred, the MA-containing solution is worked up further. To prepare crude MA, the absorption step is followed by single-stage or multistage stripping, with the crude MA being obtained at the top of the column. This stripping is carried out either under reduced pressure, preferably at from 50 to 100 mbar, or by means of nitrogen, hydrogen or a mixture of nitrogen and hydrogen as stripping gas. The absorption medium which has been largely freed of MA is obtained at the bottom of the column and is recirculated to the absorption. However, an increase in the concentration of maleic acid and fumaric acid is observed with increasing number of recirculations. Furthermore, the formation of further acidic constituents, e.g. monoalkyl phthalates and phthalic anhydride, is also observed. In addition, tar-like high boilers are also formed. WO 96/29323 describes the removal of the tar-like components and high boilers by extraction with water. In the tests reported, a degree of removal of a maximum of 50% is achieved, with the formation of emulsions being observed, especially at the very high degrees of removal, resulting in problems in phase separation.

EP-A-897 905 describes the extraction of acidic compounds by means of aqueouos alkaline solutions in the preparation of MA. According to this method, a gaseous reaction mixture comprising maleic anhydride is brought into contact with an organic solvent, at least part of the maleic anhydride is separated off from the organic solvent, part of the organic solvent remaining after the maleic anhydride has been separated off is scrubbed with an aqueous alkali solution, for example sodium hydroxide or ammonia solution, and the scrubbed organic solvent and the remaining organic solvent are returned to the absorption of the maleic anhydride from the gaseous reaction mixture. Compared to extraction using pure water, extraction with alkali is said to lead to better results. The document says nothing about problems in the phase separation in the simultaneous presence of high boilers.

A disadvantage of the processes described in the above documents is the relatively low degree of removal, in particular in the case of tar-like polymers. Difficulties in phase separation when the extracted proportion of high boilers approaches 50% are likewise disadvantageous. Another disadvantage is the fact that the aqueous phase has to be disposed of. Discharge into the wastewater system may be problematical, since the organic material in the aqueous phase has to have a prescribed degradability. Incineration suffers from drawbacks particularly when alkali metal salts are present in the aqueous phase.

Apart from the disposal problems associated with the aqueous phase, the water content of the organic phase likewise constitutes a problem. In general, a higher water content in the solvent in the absorption of MA leads to increased formation of maleic acid, so that, in addition to the extraction stage which generally consists of a cascade of mixer-settlers, there may also be a need for a vaporization step to separate off residual water.

U.S. Pat. No. 4,118,403 describes a process for purifying an organic solvent for the absorption of maleic anhydride from a gaseous mixture, in which the maleic anhydride is separated from the solvent, a substream is taken from the solvent stream, this substream if distilled and is returned to the solvent circuit. As can be seen from the figure in the document, the entire solvent stream after the maleic anhydride has been separated off in the stripping column 16 is cooled and filtered in a cooling/filtration apparatus 41. A substream is subsequently discharged via the distillation apparatus 42 and is distilled to separate off the high boilers. The distillate is then fed back into the solvent circuit.

A disadvantage of this known process is that maleic acid and fumaric acid accumulate in the solvent circuit and the acid content thus increases. The presence of acid promotes the reaction of maleic anhydride with water to form maleic acid and the yield of MA is thus decreased. These drawbacks have been confirmed in laboratory tests carried out by us.

It is an object of the present invention to avoid the disadvantages known from the prior art and in particular to avoid accumulation of acidic components in the solvent stream.

We have found that this object is achieved by a process having the features of claim 1, in which a low-boiling fraction and a high-boiling fraction are separated off from the fraction consisting essentially of purified solvent and the fraction consisting essentially of purified solvent is fed back into the solvent stream.

The present invention makes it possible to separate off not only the high boilers but also the acidic compounds maleic acid, fumaric acid, phthalic acid, etc., before the solvent is returned to the absorption of gaseous MA. This is achieved with a small outlay in terms of apparatus and without use of extraneous substances. The low-boiling fraction separated off in the process of the present invention comprises as significant components maleic acid, fumaric acid, phthalic acid and small amounts of maleic anhydride and the solvent used. The high-boiling fraction comprises as significant components tar-like products and small amounts of the solvent used. In the fraction consisting essentially of purified solvent, the solvent is present in a purity which enables this fraction to be returned directly to the solvent circuit.

The process of the present invention can be carried out continuously, semicontinuously or batchwise.

In a first, continuous embodiment of the process of the present invention, a substream of the contaminated solvent is fed to a distillation column. Here, the low-boiling acidic components maleic anhydride, maleic acid, fumaric acid and phthalic anhydride go over at the top, the tar-like components are taken off at the bottom and the largely by-product-free solvent, for example dibutyl phthalate, is obtained via the side offtake. The distillation is advantageously carried out under reduced pressure, preferably at a pressure of from 0.1 to 100 mbar, more preferably at a pressure of from 1 to 20 mbar, particularly preferably at a pressure of from 2 to 15 mbar. When using a conventional column, the purified solvent, e.g. dibutyl phthalate, is generally taken off in the stripping section. The stream taken off at the side offtake will therefore be gaseous.

The separation generally requires from about 1 to 60, in particular from about 10 to 50, theoretical plates, preferably from 15 to 40, particularly preferably from 15 to 30, theoretical plates. A definition of theoretical plates may be found, for example, in Klaus Sattler, Thermische Trennverfahren, p. 5, right-hand column, paragraph 2, ISBN 3-527-26727-1. The side offtake is advantageously located from 1 to 5 theoretical plates above the bottom, preferably from 1 to 4 theoretical plates above the bottom.

In one variant, the distillation can be carried out in a dividing wall column as described in U.S. Pat. No. 2,471,134, in EP-A-0 122 367 or by G. Kaibel, Chem. Eng. Technol. Vol. 10, 1987, pp. 92–98. In this case, the solvent, for example the dibutyl phthalate, is separated off as a liquid stream at the side offtake.

Suitable vaporizers are fouling-insensitive and easy-to-clean heat exchangers, for example falling film evaporators or thin film evaporators, forced-circulation depressurization evaporators or stirred vessels provided with, for example, an anchor stirrer going around the wall.

Owing to the possibility of solid maleic acid or fumaric acid being formed in the condenser at the top due to an increase in the concentration, the condenser at the top should be designed so as to be insensitive to formation of solids. A quench circuit or a shell-and-tube heat exchanger through which liquid trickles are useful for this purpose. The column should also be equipped with solids-insensitive internals, for example dual flow trays or sheet metal packing.

Thus, the low-boiling fraction is taken off continuously at the top of a distillation column, the high-boiling fraction is taken off continuously from the bottom of the column and the purified solvent is taken off continuously in gaseous or liquid form via the side offtake of the column in this first embodiment of the process of the present invention.

A second embodiment of the process of the present invention is likewise carried out continuously. In contrast to the first embodiment, the tar-like high boilers are here separated off in an upstream evaporator. The distillate is subsequently passed to a distillation to separate off the low-boiling acidic constituents. Here, as a difference from the first continuous embodiment, the solvent, for example dibutyl phthalate, is taken off at the bottom of the column. The evaporation in the preliminary evaporator and the distillation are advantageously carried out under a reduced pressure of, for example, from 0.1 to 100 mbar, preferably from 1 to 20 mbar, particularly preferably from 2 to 15 mbar. The separation generally requires from about 1 to 60, in particular from about 10 to 50, theoretical plates, preferably from about 9 to 37, particularly preferably from 12 to 27, theoretical plates.

Suitable upstream evaporators are fouling-insensitive and easy-to-clean heat exchangers, for example falling film evaporators or thin film evaporators, forced-circulation depressurization evaporators or stirred vessels provided with, advantageously, an anchor stirrer going around the wall. Although precipitation of solids is not to be expected to the same degree as in the preliminary evaporator, this phenomenon does also have to be taken into account in the case of the distillation column. Owing to the possibility of solid maleic acid or fumaric acid being formed in the condensor at the top due to an increase in the concentration, the condenser at the top should be designed so as to be insensitive to formation of solids. A quench circuit or a shell-and-tube heat exchanger through which liquid trickles are useful for this purpose.

Thus, the low-boiling fraction and the fraction consisting essentially of purified solvent are distilled off continuously from the high-boiling fraction, and the low-boiling fraction is separated off from the distillate via the top and the fraction consisting essentially of purified solvent is separated off at the bottom in the second embodiment of the process of the present invention which has just been described.

A third embodiment is carried out batchwise. Here, a column is superposed on a stirred vessel provided with, preferably, an anchor stirrer going around the wall. The contaminated solvent is placed in the stirred vessel. Two fractions are distilled off under reduced pressure, firstly a low-boiling fraction comprising maleic anhydride and maleic acid, fumaric acid, phthalic anhydride and solvent, for example dibutyl phthalate. As main fraction, the solvent, for example dibutyl phthtalate, goes over at the top. After this concentration by distillation, a mixture of high boilers and solvent, for example dibutyl phthalate, can be taken from the stirred vessel. The discontinuous fractionation can be achieved, for example, by reducing the pressure and/or increasing the temperature. To keep the throughput through the column uniform, the distillate can be taken off at one point, subjected to intermediate storage and fed back into the column.

The fourth embodiment of the process of the present invention is carried out semicontinuously. In contrast to variant 3, feed is introduced into the stirred vessel during distillation. The abovementioned low boilers go over at the top, while the solvent, for example dibutyl phthtalate, is taken off via the side offtake. No bottom product is taken off during the distillation and accumulates during operation. As soon as a maximum level of liquid phase is exceeded, the inlet valve is closed and the contents of the stirred vessel are drained after breaking the vacuum. However, continuous operation is in principle also possible by taking off the bottom product continually or at intervals.

The process of the present invention is preferably carried out using a solvent which has a boiling point which is higher than the boiling points of the low boilers maleic acid, fumaric acid and phthalic anhydride. Preference is given to using a solvent which has a boiling point which is 5° Kelvin higher, preferably 10° Kelvin higher, most preferably 30° Kelvin higher, than the boiling points of the low boilers maleic acid, fumaric acid and phthalic anhydride, so that these components can be separated off as low boilers. Finally, the boiling point of the solvent should be sufficiently low for it to be able to be separated off from the tar-like polymers without decomposition under an industrially feasible vacuum.

Possible solvents are dialkyl phthalates, for example those having from 2 to 8 carbon atoms in each alkyl chain. Examples which may be mentioned are dimethyl phthalate, diethyl phthalate, dipropyl phthalate, diisopropyl phthalate, dibutyl phthalate, diisobutyl phthalate, dimethyl dihydrophthalate, diethyl dihydrophthalate, dipropyl dihydrophthalate, diisopropyl dihydrophthalate, dibutyl dihydrophthalate, diisobutyl dihydrophthalate, dimethyl tetrahydrophthalate, diethyl tetrahydrophthalate, dipropyl tetrahydrophthalate, diisopropyl tetrahydrophthalate, dibutyl tetrahydrophthalate and diisobutyl tetrahydrophthalate.

However, it is also possible to use monoalkyl phthalate compounds, preferably those having from 2 to 8 carbon atoms in the alkyl chain. Examples are monomethyl phthalate, monoethyl phthalate, monopropyl phthalate, monoisopropyl phthalate, monobutyl phthalate, monoisobutyl phthalate, monomethyl dihydrophthalate, monoethyl dihydrophthalate, monopropyl dihydrophthalate, monoisopropyl dihydrophthalate, monobutyl dihydrophthalate, monoisobutyl dihydrophthalate, monomethyl tetrahydrophthalate, monoethyl tetrahydrophthalate, monopropyl tetrahydrophthalate, monoisopropyl tetrahydrophthalate, monobutyl tetrahydrophthalate and monoisobutyl tetrahydrophthalate. Further suitable solvents are, for example, dimethylbenzophenone, dichlorophenyl oxide, hexahydrophthalates and monoalkyl-substituted succinic acids having from 12 to 16 carbon atoms. A representative selection of solvents is described in WO 96/29323, which is hereby expressly incorporated by reference.

To achieve successful purification of the solvent, it is generally sufficient for a substream of the circulating solvent to be discharged. In general, this substream comprises from about 0.2 to 1% by weight, preferably from 0.3 to 0.7% by weight, of the total amount of solvent.

The term "essentially" used here in the context of the fraction consisting "essentially" of purified solvent means that the fraction consists of solvent which has been purified to a substantial extent. The purity of the solvent which has been purified in this way can vary. It should be such that no appreciable accumulation of acidic constituents takes place in the solvent present in the absorption circuit during operation, since otherwise there is a risk of the yield of MA decreasing. The purity of the solvent purified in the substream is advantageously at least 95% by weight or higher, preferably at least 97% by weight, particularly preferably at least 99% by weight.

When monoalkyl or dialkyl phthalates are used, the purity is preferably at least 97% by weight, particularly preferably at least 99% by weight.

The invention is illustrated by the following examples.

EXAMPLE 1

10.0 kg/h of a stream composed of 0.5% by weight of MA, 1.0%, by weight of maleic acid, 1.0% by weight of fumaric acid, 0.4% by weight of tar-like high boilers, 1.0% by weight of phthalic anhydride and 96.1% by weight of dibutyl phthalate were fed into a column having 20 theoretical plates at theoretical plate no. 10 (counted from the top of the column). At a pressure of 10 mbar at the top, a stream of 0.8 kg/h was taken off at the top. About 4 kg/h of runback were returned to the top of the column. The product obtained at the top was composed of 6.3% by weight of MA, 56% by weight of dibutyl phthalate and 12.5% by weight each of maleic acid and fumaric acid, together with phthalic anhydride (PA). At the bottom, 0.1 kg/h of a mixture consisting of 73% by weight of dibutyl phthalate and 27% by weight of high boilers was taken off at 228° C. At the side offtake, which was located at the seventeenth (counted from the top) theoretical plate, 9.1 kg/h of dibutyl phthalate having a purity of 99.8% were obtained. The recovery of dibutyl phthalate was 95%.

EXAMPLE 2

100 kg of a mixture composed of 0.5% by weight of MA, 1.0% by weight of maleic acid, 1.0% by weight of fumaric acid, 0.4% by weight of tar-like high boilers, 1.0% by weight of phthalic anhydride (PA) and 96.1% by weight of dibutyl phthalate were placed in a stirred vessel fitted with a superposed column having 20 theoretical plates. The apparatus was subsequently evacuated to 10 mbar. By means of a swivelling funnel, a substream of the distillate was returned to the column. At a reflux ratio of 8, 10 kg of a first fraction were firstly taken off. During distillation, the temperature at the top increased from 103° C. to 190° C. The distillate was collected in a vessel and had the following composition: MA and maleic acid: 13% by weight; fumaric acid: 19% by weight; phthalic anhydride: 10% by weight; dibutyl phthalate: 68% by weight. The reflux ratio was subsequently changed to 2 and 86 kg of dibutyl phthalate having a purity of 99.6% were taken off at 190° C. 4 kg of dibutyl phthalate containing about 10% by weight of high boilers remained in the stirred vessel. The recovery of dibutyl phthalate was 86%.

We claim:

1. A process for purifying an organic solvent for the absorption of maleic anhydride from a gaseous mixture, where the maleic anhydride is separated from the solvent, a substream is taken from the solvent stream and this substream is distilled and returned to the solvent circuit, wherein a low-boiling fraction and a high-boiling fraction are separated off from the fraction consisting essentially of purified solvent and the fraction consisting essentially of purified solvent is fed back into the solvent stream.

2. A process as claimed in claim 1, wherein the distillation is carried out at a pressure of from 0.1 to 100 mbar.

3. A process as claimed in claim 1, wherein the low-boiling fraction is taken off continuously at the top of a distillation column, the high-boiling fraction is taken off continuously from the bottom of the column and the purified solvent is taken off continuously in gaseous or liquid form via the side offtake of the column.

4. A process as claimed in claim 1, wherein the low-boiling fraction and the fraction consisting essentially of purified solvent are distilled off continuously from the high-boiling fraction, and the low-boiling fraction is separated off from the distillate via the top and the fraction consisting essentially of purified solvent is separated off at the bottom.

5. A process as claimed in claim 1 which is carried out batchwise or semicontinuously.

6. A process as claimed in claim 1, wherein the organic solvent used has a boiling point which, at atmospheric pressure, is at least 30° Kelvin above the boiling point of the low-boiling fraction.

7. A process as claimed in claim 1, wherein the distillation is carried out using a dividing wall column.

8. A process as claimed in claim 1, wherein the distillation is carried out at a pressure of from 1 to 20 mbar.

* * * * *